(12) United States Patent
Devonec

(10) Patent No.: US 6,949,083 B2
(45) Date of Patent: Sep. 27, 2005

(54) THERAPEUTIC DEVICE FOR THE SELECTIVE CYTOREDUCTION TREATMENT OF AN OBSTRUCTION IN A NATURAL LUMEN OR PASSAGE OF THE HUMAN OR ANIMAL BODY

(76) Inventor: Marian Devonec, 81 avenue des Balmes, Miribel (FR)

( * ) Notice: Subject to any disclaimer, the term of this patent is extended or adjusted under 35 U.S.C. 154(b) by 263 days.

(21) Appl. No.: 09/826,207

(22) Filed: Apr. 5, 2001

(65) Prior Publication Data

US 2001/0041883 A1 Nov. 15, 2001

Related U.S. Application Data

(62) Division of application No. 08/765,199, filed as application No. PCT/FR95/00869 on Jun. 29, 1995, now Pat. No. 6,238,368.

(30) Foreign Application Priority Data

Jul. 13, 1994 (FR) ............................................. 94 08933

(51) Int. Cl.[7] ............................................. A61M 31/00
(52) U.S. Cl. .................... 604/93.01; 604/517; 604/104; 623/23.66; 623/23.64; 623/23.7
(58) Field of Search .............................. 604/93.01, 265, 604/48, 104, 96.01, 266, 523, 514–517, 8, 105–109, 101.01; 606/192, 194, 198, 191, 193; 623/1.11, 23.64, 23.66–23.68, 23.7, 23.71, 23.73–23.76, 1.15, 1.16, 1.42; 424/422–426; 514/411

(56) References Cited

U.S. PATENT DOCUMENTS 4,156,067 A 5/1979 Gould
4,660,560 A 4/1987 Klein
4,676,782 A 6/1987 Yamamoto et al.

(Continued)

FOREIGN PATENT DOCUMENTS

| EP | 0 164 241 | 12/1985 |
| EP | 0 274 846 | 7/1988 |
| WO | 80/01460 | 7/1980 |
| WO | 89/03232 | 4/1989 |
| WO | 94/18907 | 9/1994 |

OTHER PUBLICATIONS

Fair, William R., "Internal Urethrotomy Without a Catheter: Use of a Urethral Stent," *The Journal of Urology*, vol. 127, p. 675–676, Apr. 1982.

Primary Examiner—Cris L. Rodriguez
(74) Attorney, Agent, or Firm—Oliff & Berridge, PLC

(57) ABSTRACT

Therapeutic device intended for the selective cytoreductive treatment of an obstruction in a natural lumen or passage of the human or animal body, the lumen being obstructed by the effect of a local cell proliferation, the device including a tubular element, in particular of cylindrical shape, intended to be placed in the natural lumen and sufficiently flexible to conform to the natural lumen, but sufficiently rigid to maintain an artificial channel in the lumen. The tubular element supports lengthwise a medicinal sleeve which is intended to come into line with, and into contact with, the obstruction once the natural lumen has been intubated, and is designed to deliver locally, at least in its outer surface portion, at least one therapeutic agent which is cytoreductive, in particular cytotoxic, through contact with the cells under whose effect the lumen is obstructed.

24 Claims, 7 Drawing Sheets

U.S. PATENT DOCUMENTS

| | | | |
|---|---|---|---|
| 4,768,507 A | 9/1988 | Fischell et al. | |
| 4,895,566 A | 1/1990 | Lee | |
| 4,932,938 A | 6/1990 | Goldberg et al. | |
| 4,973,301 A | 11/1990 | Nissenkorn | |
| 4,990,155 A | 2/1991 | Wilkoff | |
| 4,994,066 A | 2/1991 | Voss | |
| 5,041,092 A | 8/1991 | Barwick | |
| 5,059,169 A | 10/1991 | Zilber | |
| 5,160,341 A * | 11/1992 | Brenneman et al. | 606/198 |
| 5,222,971 A | 6/1993 | Willard et al. | |
| 5,234,456 A | 8/1993 | Silvestrini | |
| 5,246,445 A | 9/1993 | Yachia et al. | |
| 5,258,020 A | 11/1993 | Froix | |
| 5,269,802 A | 12/1993 | Garber | |
| 5,282,823 A | 2/1994 | Schwartz et al. | |
| 5,286,254 A | 2/1994 | Shapland et al. | |
| 5,304,121 A | 4/1994 | Sahatjian | |
| 5,322,501 A | 6/1994 | Mahmud-Durrani | |
| 5,342,348 A | 8/1994 | Kaplan | |
| 5,419,760 A | 5/1995 | Narciso, Jr. | |
| 5,429,634 A | 7/1995 | Narciso, Jr. | |
| 5,441,516 A | 8/1995 | Wang et al. | |
| 5,464,650 A | 11/1995 | Berg et al. | |
| 5,499,994 A | 3/1996 | Tihon et al. | |
| 5,545,208 A * | 8/1996 | Wolff et al. | 623/1.22 |
| 5,549,559 A | 8/1996 | Eshel | |
| 5,562,622 A | 10/1996 | Tihon | |
| 5,588,965 A | 12/1996 | Burton et al. | |
| 5,599,306 A | 2/1997 | Klein et al. | |
| 5,601,591 A | 2/1997 | Edwards et al. | |
| 5,609,629 A | 3/1997 | Fearnot et al. | |
| 5,626,562 A | 5/1997 | Castro | |
| 5,667,486 A | 9/1997 | Mikulich et al. | |
| 5,674,192 A * | 10/1997 | Sahatjian et al. | 604/28 |
| 5,716,981 A * | 2/1998 | Hunter et al. | 514/449 |
| 5,733,303 A | 3/1998 | Israel et al. | |
| 5,738,654 A | 4/1998 | Tihon | |
| 5,766,209 A | 6/1998 | Devonec | |
| 5,811,447 A * | 9/1998 | Kunz et al. | 514/411 |
| 5,830,179 A | 11/1998 | Mikus et al. | |
| 5,876,417 A | 3/1999 | Devonec et al. | |
| 5,879,697 A | 3/1999 | Ding et al. | |

* cited by examiner

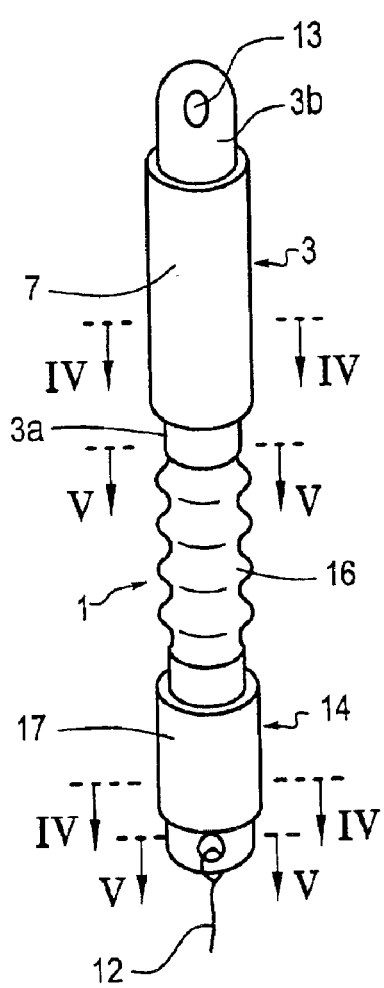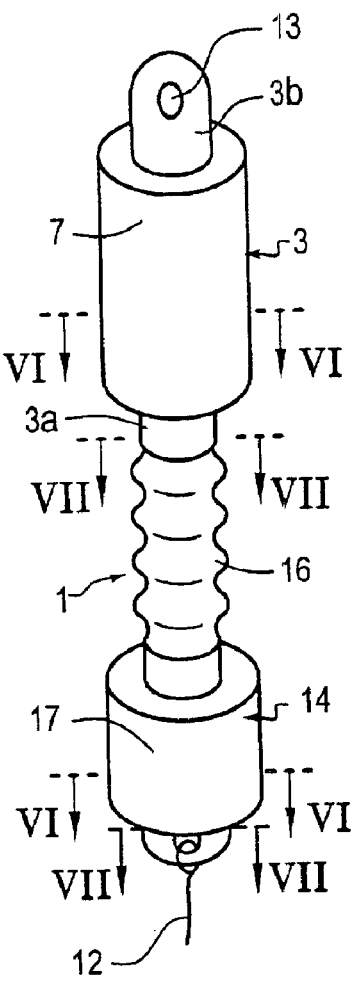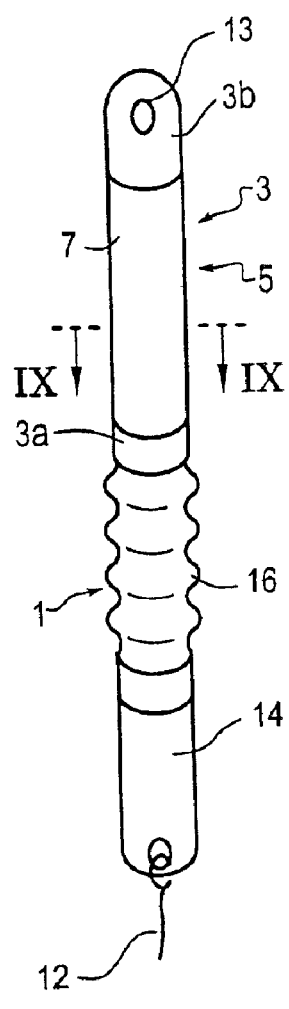
Fig. 2　　　　Fig. 3　　　　Fig. 8
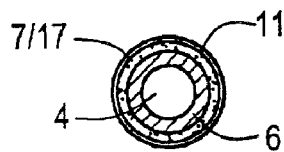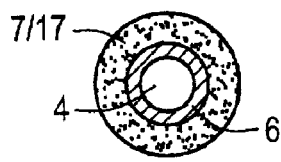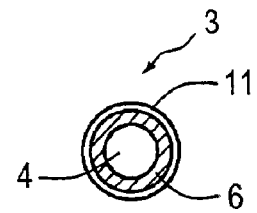
Fig. 4　　　　Fig. 6　　　　Fig. 9
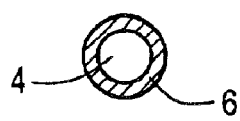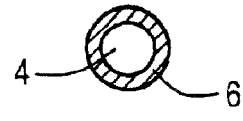
Fig. 5　　　　Fig. 7

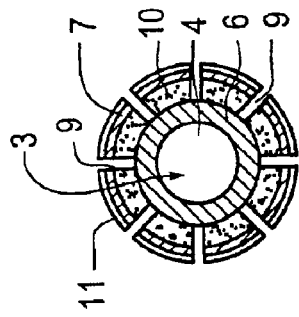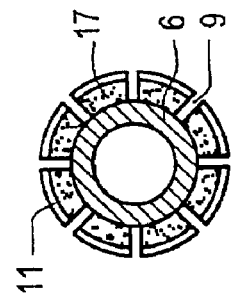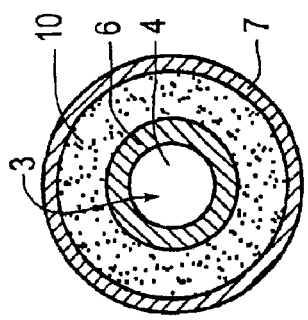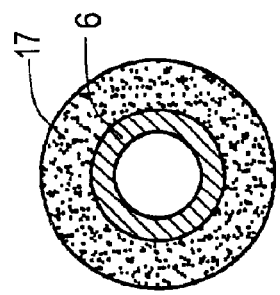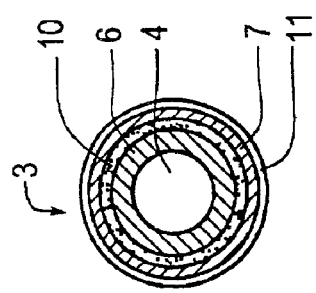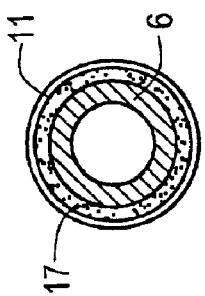

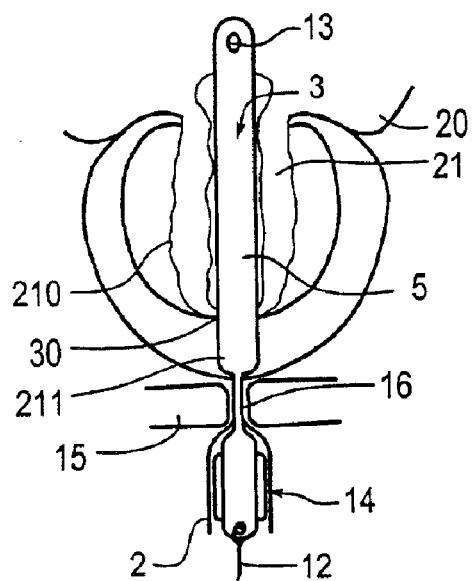
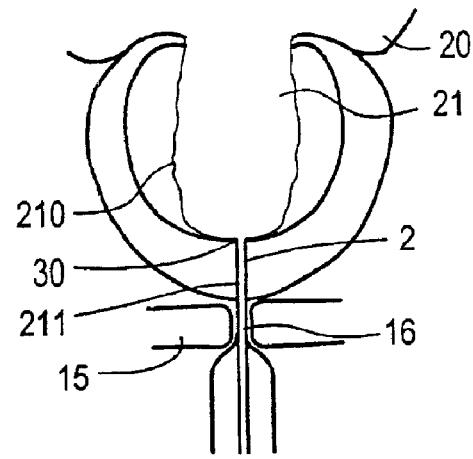
Fig. 23  Fig. 24
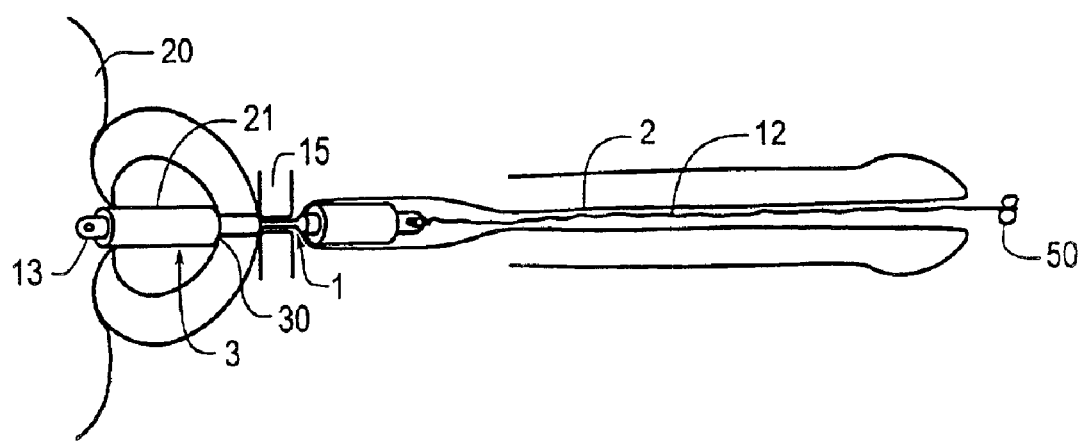
Fig. 25

THERAPEUTIC DEVICE FOR THE SELECTIVE CYTOREDUCTION TREATMENT OF AN OBSTRUCTION IN A NATURAL LUMEN OR PASSAGE OF THE HUMAN OR ANIMAL BODY

This is a divisional of application Ser. No. 08/765,199, filed Feb. 10, 1997, now U.S. Pat. No. 6,238,368, which is a 371 of PCT/FR95/00869, filed Jun. 29, 1995, pending. The entire disclosure of the prior application is hereby incorporated by reference herein in its entirety.

BACKGROUND OF THE INVENTION

1. Field of the Invention

The present invention relates to the treatment of a natural lumen or passage located in a filled area, in particular in a solid organ of the human or animal body, which lumen provides for the transit or circulation of a fluid, in particular a body fluid, which is either liquid or gaseous, this natural lumen or passage being obstructed by the effect of a local cell proliferation.

The urinary passages, and in particular the urethra, constitute examples of natural lumina within the meaning of the present invention.

The expression "local cell proliferation" is understood to mean any biological process, for example of the benign or malignant tumor type, leading locally to a tissue excess, either organized or unorganized, and provoking an obstruction, or obstructing the natural lumen or passage in question, at the site where said proliferation develops. Benign prostatic hypertrophy, or prostatic adenoma, constitutes one example of an obstructive cell proliferation of this nature.

The present invention will be introduced, defined and described, by way of non-limiting example, with reference to the treatment of acute or chronic prostate obstructions in man.

2. Description of Related Art

It is presently known to treat prostate obstruction by mechanical means, that is to say without curative action vis-à-vis the cause of the obstruction, and for this purpose various intraurethral prostheses have been described or are available on the market. Reference will be made, by way of example, to the prosthesis which is described in document WO-A-94/18907.

Such prostheses, which are implanted permanently or temporarily, provide for only a palliative treatment of the prostate obstructions.

These prostheses may be poorly tolerated by the patient on account of their purely mechanical action, these prostheses being foreign bodies which are left in place permanently, or else temporarily but repeatedly. In some cases there may be a risk of infection and of not inconsiderable migration. These prostheses, when they are permanent, present a risk of obstruction, either by incrustation (deposition of crystals contained in the urine) or by hyperplasia inside the prosthesis, as a reaction to the foreign body which the prosthesis represents; this hyperplasia can go so far as to obstruct certain permanent prostheses.

SUMMARY OF THE INVENTION

The object of the present invention is to remedy these disadvantages.

More specifically, the invention relates to a treatment, of an obstruction in a natural lumen, which is limited in time, is of the curative type, and has a local and selective action.

In accordance with the present invention, a novel therapeutic treatment device is proposed which can be implanted in the natural lumen or passage to be treated and which comprises:

in a manner known per se, a non-biodegradable tubular element which is designed to be placed and retained, in a substantially self-stabilizing manner, in the natural lumen being treated; this element, which is preferably of cylindrical shape, is at one and the same time sufficiently flexible to conform to the natural lumen lying against its wall, and sufficiently rigid to maintain an artificial channel, and hence a circulation, in the natural lumen;

in a novel manner, a medicinal sleeve which is supported by the tubular element and which is positioned along the length of, and around, the latter, so as to come into line with, and into direct contact with, the obstruction once the natural lumen has been intubated with said tubular element; this sleeve comprises or incorporates a therapeutic agent which is cytoreductive, in particular cytotoxic, specifically vis-à-vis the cells of said local cell proliferation, essentially through simple, superficial and solid tissue contact with said cells; this sleeve is moreover designed to deliver this therapeutic agent at least in its outer portion.

According to the present invention, the expression "supported by" is understood to mean that the medicinal sleeve is present on the tubular element, either visibly and/or distinct from the latter, or such that it cannot be seen, being held or incorporated in said tubular element, in its material or its constituent elements, over a length and/or at a position which are predetermined by said tubular element.

According to the present invention, the term "therapeutic" is understood to mean any treatment of a medicinal and in particular chemical type, in isolation, or complementing another treatment, and permitting local and selective reduction of the obstruction of the natural lumen or passage in question, whether it be the cells lining the wall of said lumen, or the cells situated deep behind these cells. According to the present invention, this treatment of the medicinal type is facilitated or supplemented by a treatment of the mechanical type, the aim being to maintain during treatment, and then to reestablish, the flow in the natural lumen which is disrupted or prevented as a result of the obstruction of this same lumen.

By virtue of the invention, once the therapeutic device has been arranged in the obstructed natural lumen, the medicinal sleeve selectively delivers the cytoreductive agent to the obstructed part of the wall of the natural lumen, and then to the subjacent cell proliferation. As a consequence of this delivery, there is a gradual erosion of the obstructed part of the wall of the natural lumen being treated, then of the subjacent tissue responsible for the compression or obstruction of this same lumen, along a front which has the shape of a cylindrical envelope, progressing radially outward, in a manner substantially concentric with the medicinal sleeve. This thus leads to the formation of a channel through the lumen being treated, which channel has a transverse dimension at least greater than the normal transverse dimension of the same lumen. As soon as the contact between the outer surface portion of the medicinal sleeve and the surrounding tissues or cells ceases, the cytoreductive action ceases, it being understood that the latter action can also cease by means of the therapeutic device according to the invention simply being withdrawn from the natural lumen in which it has been positioned.

All in all, this leads to a pharmaceutically induced modeling of the natural lumen being treated, leaving behind a channel which has as it were been "molded" on the tubular element of the therapeutic device according to the invention.

Consequently, as a result of a dual action—both medicinal and mechanical—of the device according to the invention, it is thus possible to construct a new channel in the obstructed part of any natural lumen, this channel having substantially the same axis and the same shape as the tubular element which has been used to shape it. Once this new channel has been created, the device according to the invention is withdrawn, and the new duct thus obtained acquires an epithelium from the upstream and downstream parts of the natural lumen not being treated with the medicinal sleeve.

Although the following is one embodiment of the invention among others, it is preferable, on the one hand, for the tubular element to comprise an internal core, which is cylindrical for example, and made of a biocompatible material, in particular a relatively smooth and soft material, for example silicone rubber, and, on the other hand, for the medicinal sleeve, distinct from the tubular element and covering the latter, to be arranged outside the core, and to comprise a biologically compatible substrate or support which incorporates the cytoreductive therapeutic agent.

A therapeutic device according to the invention also affords the following important advantages.

The cytoreductive therapeutic agent is delivered in situ, and specifically to the cell proliferation generating or having generated the obstruction in the natural lumen. Such a local administration of a cytoreductive active principle considerably reduces the side effects or morbidity compared to administration of the same active principle systemically, for example by the oral route, as regards the treatment of benign hypertrophy.

The cytoreductive effect is strictly limited to the obstructed part, and to the exclusion of the surrounding zones of the natural lumen which remain isolated from the action of the cytoreductive therapeutic agent, since the corrosive effect of said agent on the surrounding tissues is produced only by mechanical or solid contact, without a liquid intermediary.

The products of tissue or cell degradation are eliminated along the natural lumen, from which the obstruction has been removed. In general, these products or waste substances can be diluted and evacuated with the body fluid circulating in the natural lumen being treated.

A therapeutic device according to the invention can be put in place in the lumen being treated in a simple and non-traumatic way.

As regards the therapeutic treatment of the prostatic portion of the urethra in man, an intraurethral therapeutic device according to the invention comprises two tubular elements which are intended to be arranged in the urethra, on either side respectively of the sphincter, and are attached to one another by a flexible and deformable connection means which is intended to be held in the orifice of the sphincter. The upper tubular element supports the medicinal sleeve in the prostatic portion of the urethra, and the lower tubular element does not include a medicinal sleeve. In particular, the medicinal sleeve is positioned, in relation to the upper tubular element, from a so-called lower end, situated above the bottom end (in relation to the implanted position) of the upper tubular element, for example at approximately 10 mm from this bottom end, to a so-called upper end, situated set back from the top end of the upper tubular element, for example at a distance of between 10 and 15 mm from this top end.

By virtue of these supplementary arrangements for an intraurethral device, the cytoreductive effect is limited to the obstruction zone which extends from the verumontanum to the neck of the bladder, and in particular to the segment of the prostatic urethra superior to the verumontanum.

The part of the upper tubular element, capable of protruding into the bladder once the implant has been put in place, is not dangerous insofar as this end, which may come into contact with the bladder wall, is deprived of cytoreductive agent over a certain length.

An intraurethral therapeutic device according to the invention is thus fundamentally distinguished from the intraurethral device which is described in document WO-A-8 903 232 in that:

it makes it possible to treat an obstructed anatomical lumen or duct, in this case the urethra, present in a solid or filled organ, in this case the prostate, and not in a general manner an anatomical cavity, in this case the bladder, filled with a liquid serving to diffuse the therapeutic agent;

the support for the therapeutic agent or active principle used is arranged along and around the tubular element, and not at the free end of the latter, which end, according to the present invention, remains deprived of said therapeutic agent;

the action of the therapeutic agent is exerted by simple, superficial and solid tissue contact with the cells which are to be destroyed, and not by diffusion in a liquid, which in turn bathes the wall which is to be treated; by way of an example, but not exclusively, any therapeutic agent which is not hydrosoluble can be used according to the present invention.

And a therapeutic device according to the invention is fundamentally distinguished from the device which is described in document EP-A-0 164 241 in that the tubular element is designed to be self-stabilizing, and not free in an anatomical cavity, such as the rumen of a ruminant, and to ensure the circulation of a fluid within, and not to contain a biodegradable block in which the therapeutic agent is incorporated.

All these structural and functional differences compared to the prior art identified above justify in particular the fundamental innovation afforded by the present invention, and residing in particular in the idea of pharmaceutically induced modeling of a natural duct or lumen of a solid or filled organ, as described and defined hereinabove.

BRIEF DESCRIPTION OF THE DRAWINGS

The present invention is now described with reference to the attached drawing, in which:

FIGS. 2 and 3 each represents a therapeutic device according to the present invention, in a frontal view, with its upstream end at the top and its downstream end at the bottom; FIG. 2 is in its configuration before implantation, that is to say ready for use, and FIG. 3 is in its configuration after implantation and activation, that is to say in the urethra, although the urethra is not represented in FIG. 3;

FIG. 4 represents a cross-sectional view of the device represented in FIG. 2, along the sectional plane IV—IV, taken through the upper and lower tubular elements, respectively, before implantation;

FIG. 5 represents a cross-sectional view of the device represented in FIG. 2, along the sectional plane V—V, taken through the lower and upper tubular elements, respectively;

FIG. 6 represents a cross-sectional view of the device represented in FIG. 3, after implantation and activation, along the sectional plane VI—VI, taken through the lower and upper tubular elements, respectively, of the device;

FIG. 7 represents an axial section of the device represented in FIG. 3, along the sectional plane VII—VII, taken through the lower and upper tubular elements, respectively, of the device;

FIG. 8 represents, in the manner of FIG. 2, another embodiment of a device according to the invention;

FIG. 9 represents an axial section of the device represented in FIG. 8, along the sectional plane IX—IX;

FIGS. 12 and 13 represent two cross sections of a variant embodiment of a device represented in FIG. 10, before implantation, along the sectional planes XII—XII and XIII—XIII, respectively, identified in FIG. 10;

FIGS. 14 and 15 represent cross-sectional views of the device represented in FIGS. 12 and 13, after implantation and activation, along the sectional planes XIV—XIV and XV—XV, respectively, identified in FIG. 11;

Figure 10:
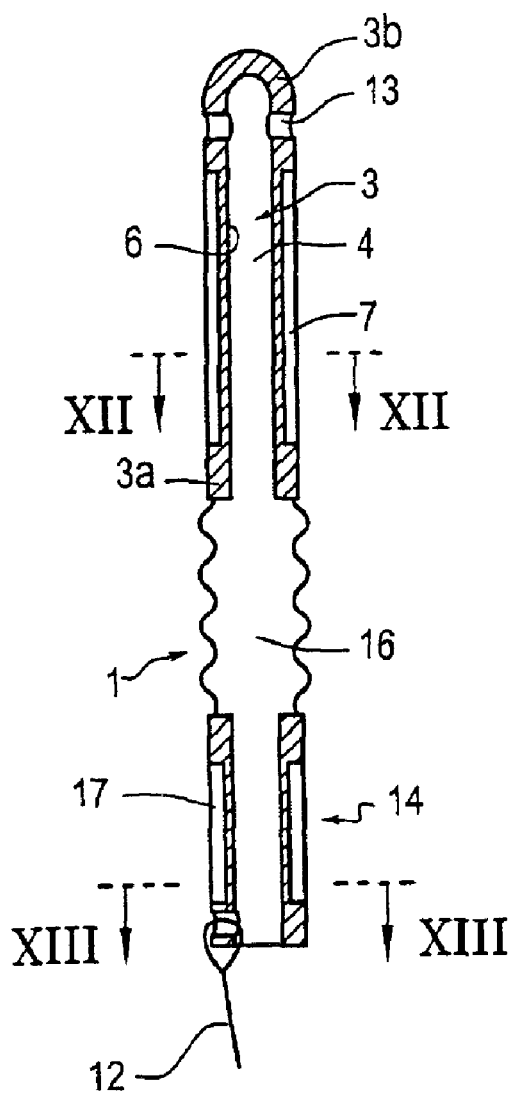
FIGS. 10 and 11 represent, in axial section, another embodiment of a therapeutic device according to the present invention, before implantation, and, respectively, after implantation and activation in the urethra, the urethra not being represented.
Figure 11:
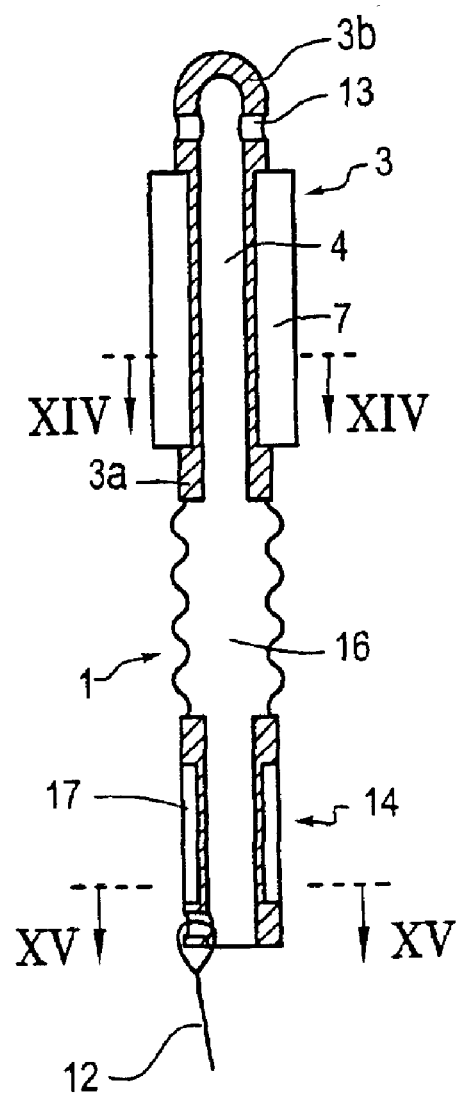
Figure 18:
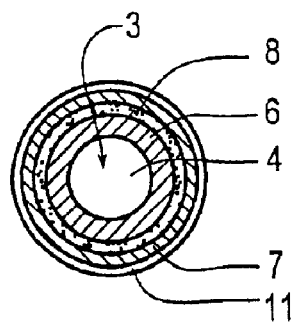
Figure 19:
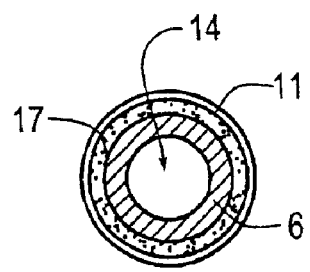
Figure 26:
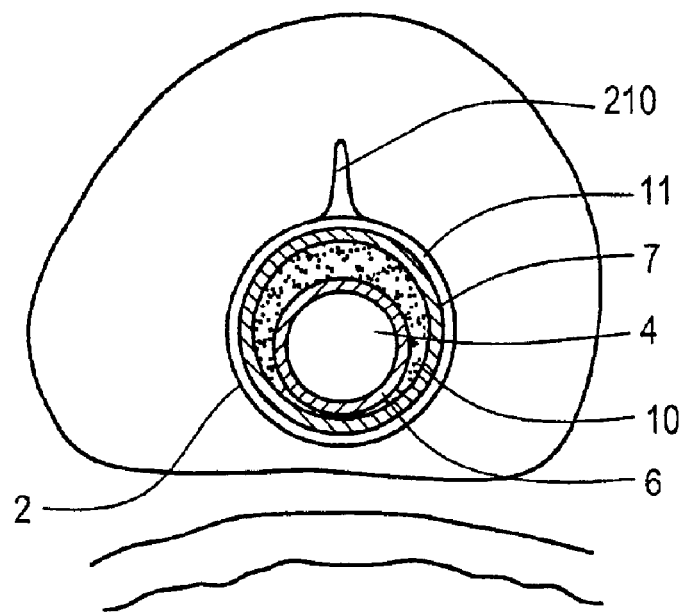
Figure 27:
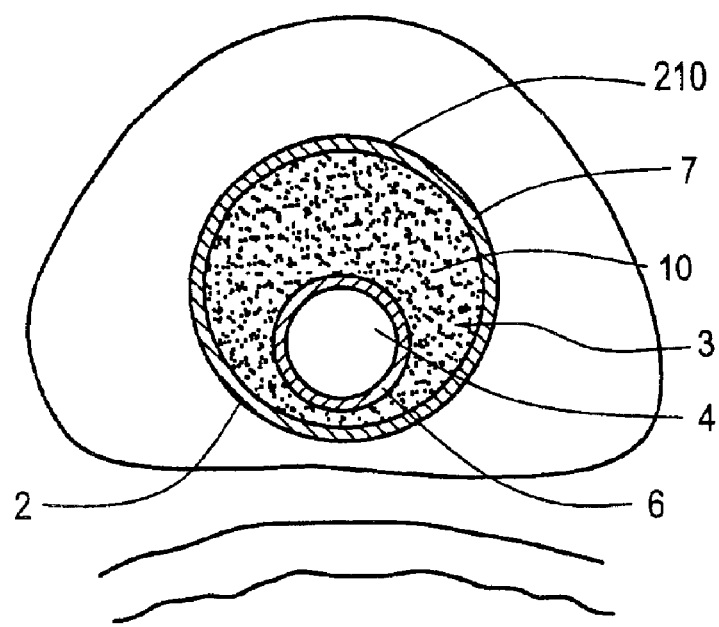

for a variant embodiment of the therapeutic device represented in FIGS. 12 to 15, FIGS. 16 and 17 represent views in axial section before implantation, along the sectional planes XII—XII and XIII—XIII, respectively, identified in FIG. 10;

in relation to the sectional planes XII—XII and XIII—XIII, respectively, identified with reference to FIG. 10, FIGS. 18 and 19 represent axial views of another embodiment of a therapeutic device according to the invention, before implantation;

FIGS. 20 to 24 represent, diagrammatically and in a frontal view, the urethra before implantation (FIG. 20), the mode of action of a therapeutic device according to the invention in position (FIGS. 21 to 23), and the urethra after withdrawal of the same device (FIG. 24);

FIG. 25 represents, in the implanted position in vivo, a therapeutic device according to the invention, represented with its withdrawal or securing thread;

FIGS. 26 and 27 represent in vivo, and in cross section, along the sectional planes XII—XII of FIG. 10 and XIV—XIV of FIG. 11, respectively, another embodiment of a therapeutic device according to the invention, before activation of the device (FIG. 26), and after activation of the device (FIG. 27).

DETAILED DESCRIPTION OF PREFERRED EMBODIMENTS

Figure 1:
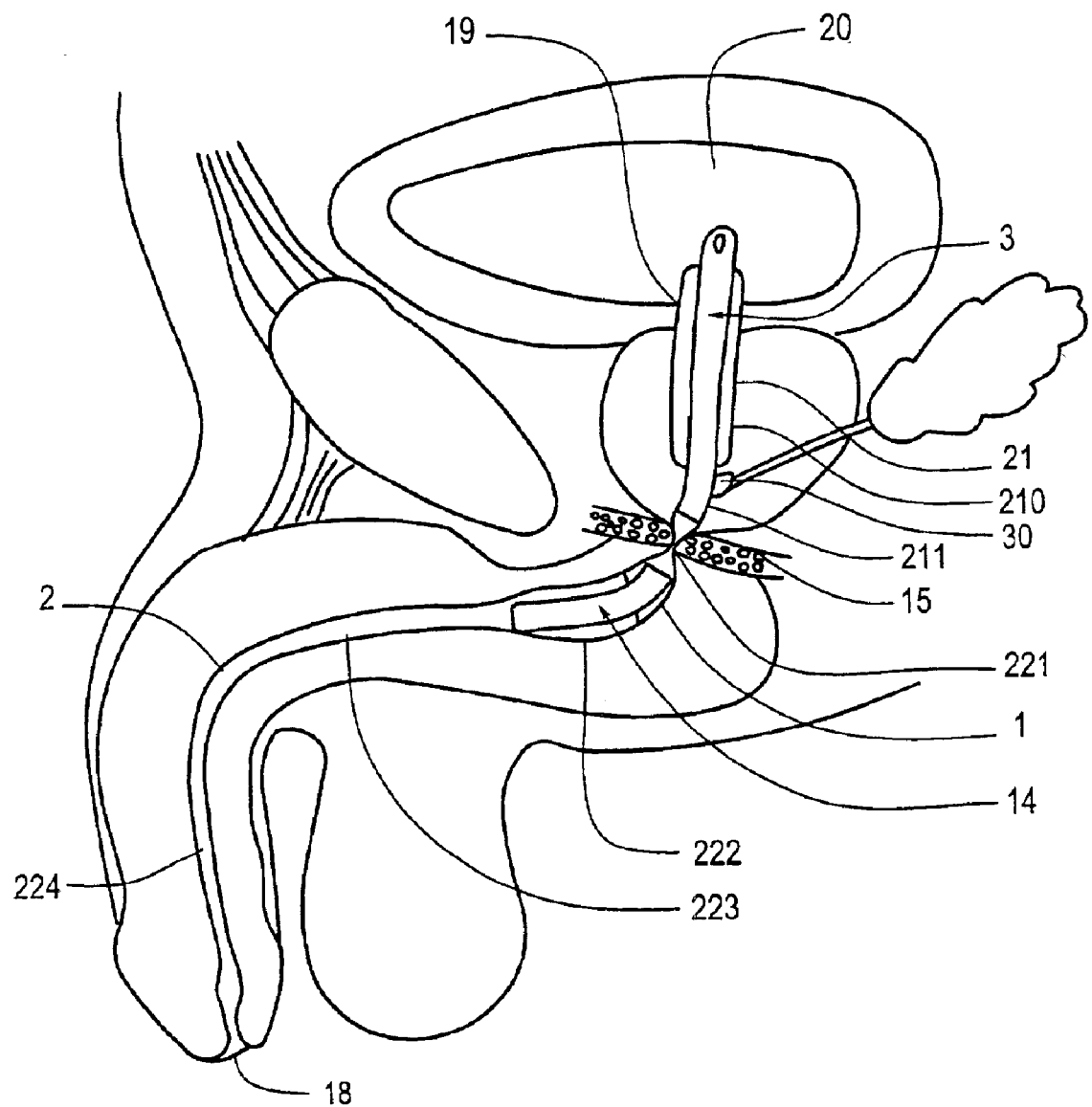
FIG. 1 represents a sagittal anatomical section of the urinary passages of the human male's; a therapeutic device according to the present invention is represented in this section, in position in the urethra.

In accordance with FIG. 1, the urethra 2 extends upward from the urinary meatus 18 to the neck 19 of the bladder 20. Above the striated muscular sphincter 15, the urethra comprises a prostatic portion 21, consisting of a prostatic segment 210 superior to the verumontanum, and of a prostatic segment 211 inferior to the verumontanum, these segments being situated on either side of said verumontanum 30 of the prostate. Below the sphincter is, the urethra comprises, in the direction toward the meatus 18, the membranous segment 221, the bulbar segment 222, the perineal segment 223, and finally the penile segment 224.

As a consequence of any adenoma which has developed in the area of the prostatic portion, the latter is susceptible to obstruction, so that a therapeutic device according to the description given hereinbelow must be put in place in the portion 21.

In accordance with FIGS. 2 and 3, this intraurethral therapeutic device 1 comprises, in a general manner, two tubular elements 3 and 14 which are intended to be arranged in the urethra 2 on either side, respectively, of the sphincter 15 and to be attached to one another by a flexible and deformable connection means 16 consisting of a flexible and elastic sleeve which is intended to be held in the orifice of the sphincter 15. The flexible sleeve 16 is in continuity of flow with the tubular elements 3 and 14.

The upper tubular element 3, which is intended to be placed and to be held in the prostatic portion 21 of the urethra, supports and is covered by a medicinal sleeve 7 which is positioned along the length of, and around, said tubular element 3. Consequently, when this tubular element 3 is arranged in the prostatic portion 21 of the urethra, the medicinal sleeve 7 comes into line with, and into direct contact with, the prostatic obstruction. This medicinal sleeve 7 comprises a therapeutic agent which is cytoreductive, specifically vis-à-vis the cells of the prostatic cell proliferation, essentially through simple, superficial and solid tissue contact with said cells. The sleeve 7 is furthermore designed, especially as regards its support, to deliver this therapeutic agent in its outer surface portion; this surface delivery of the therapeutic agent can be obtained in all appropriate ways familiar to the skilled expert, for example quasi-instantaneously, or preferably slowly, in a delayed manner or gradually, by adapting the nature and/or the composition of the substrate of the medicinal sleeve, serving as it were as an excipient for the therapeutic agent proper.

The other, lower, tubular element 14 does not have a therapeutic sleeve, and consequently does not contribute to any therapeutic treatment of the urethra below the sphincter.

The tubular elements 3 and 14, for example of cylindrical shape, are sufficiently flexible to conform to the urethra, in the implanted position, but are sufficiently rigid to maintain an artificial channel 4 in the urethra, ensuring the circulation of the urine.

The therapeutic sleeve 7 is positioned, in relation to the upper tubular element 3 along its length, so that a so-called lower end is situated above the bottom end 3a of the upper tubular element 3, for example approximately 10 mm from this bottom end, and a so-called upper end is situated set back from, and below, the top end 3b of the upper tubular element 3, for example at a distance of between 10 and 15 mm from the abovementioned top end.

As is shown in FIGS. 2 and 3, the top end 3b of the upper tubular element 3 is blind, and is perforated 13 in order to ensure the passage of the urine from the bladder 20.

The tubular elements 3 and 14 each comprise a core 6 in the form of a tube made of a biocompatible but non-biodegradable material, in particular a relatively smooth and soft material, for example a silicone rubber.

The medicinal sleeve 7 covers the internal core 6 of the upper tubular element 3 and is arranged on the outside of the latter. This sleeve 7 comprises a biologically compatible substrate incorporating the cytoreductive therapeutic agent. This substrate is expandable and, if appropriate, radially compressible, so that in the dry state, and before implantation of the device, it adopts a gathered-in and compact, non-expanded configuration, and after implantation and activation, in the wet or moist state, it adopts an expanded configuration; these two configurations, namely non-expanded and expanded, respectively, are represented in FIGS. 2 and 4 and in FIGS. 3 and 6, respectively. The substrate of the sleeve 7 is, for example, a hydrophilic material, which is expandable under the effect of the biological fluids present or circulating in the urethra. Examples of an expandable and hydrophilic substrate of this kind are the various cellulose materials already used in the medical sector.

Similarly, but without cytoreductive therapeutic agent, the lower tubular element 14 supports and is surrounded by an outer sleeve 17 covering the internal core 6 of said element 14, expandable and, if appropriate, radially compressible, and consisting, for example, of the same hydrophilic and expandable, and, if appropriate, biodegradable material as that used in the composition of the medicinal sleeve 7.

The medicinal sleeve 7 is covered at the outset, that is to say before the implantation of the device, by a protective surface envelope 11 which can be broken down and/or biodegraded by tissue contact in situ with the obstructed portion of the urethral duct. More precisely, this envelope 11 is capable of retaining the medicinal sleeve 7 in the non-expanded state before the implantation of the device, and then of breaking down, leaving the sleeve 7 free to expand; it is this which is represented in FIGS. 2 and 4 and in FIGS. 3 and 6, respectively. Exactly in the same way, a protective surface envelope 11 which can be broken down can be used to contain and then to free the outer expandable sleeve 17 surrounding the lower tubular element 14.

As is shown in FIGS. 2 and 3, but also in FIG. 25, a withdrawal or securing thread 12 is secured to the downstream end of the device, and more precisely to the bottom end of the lower tubular element 14. The downstream end of the thread 12 can moreover be provided with a viewing indicator 50, for example a bead secured on the thread 12, as is shown in FIG. 25.

The medicinal sleeve 7 can incorporate, in addition to the cytoreductive agent, a bacteriostatic agent, and, if appropriate, all other agents necessary for a therapeutic or surgical intervention, for example an agent opaque vis-à-vis X-rays. The cytoreductive agent is- chosen preferably, but not exclusively, from among the antimitotic agents, cytolytic agents, enzymes, hormones, antienzymes, and metal salts, for example silver salts.

The therapeutic device represented in FIGS. 8 and 9 differs from that represented with reference to FIGS. 2 to 7 in that the sleeves 7 and 17 merge with the tubular elements 3 and 14, respectively, and more precisely their core 6 as defined above.

The medicinal sleeve 7 is obtained by direct incorporation, at least at the surface, of the cytoreductive therapeutic agent in the material, for example the silicone rubber, of the core 6 of the tubular element 3, in a biologically active, elongate zone 5, materialized or not.

The protective surface envelope 11 is retained, however, in order to prevent release of the cytoreductive agent in any part of the therapeutic device not in contact with the obstruction, for example protruding inside the bladder.

The therapeutic device represented in FIGS. 10 and 11 differs from that represented in FIGS. 2 to 7 in that:

the substrate of the medicinal sleeve 7, in its radially non-expanded configuration, presents an outer surface inscribed within the remainder of the outer surface of the upper tubular element 3; and in the expanded position, represented in FIG. 11, the outer surface of the medicinal sleeve 7 emerges from the outer surface of the same tubular element 3;

the same configuration, non-expanded and then expanded, is used for the outer sleeve 17 of the lower tubular element 14.

The therapeutic device represented in FIGS. 12 to 15 differs from that represented with reference to FIGS. 2 to 7 in that the medicinal sleeve 7 is limited to a cylindrical surface layer of the substrate, while the remainder of the latter constitutes an expandable connection sleeve 10 interposed between the core 6 of the tubular element 3 and the medicinal sleeve 7 proper. The lower tubular element 14 remains unchanged.

The therapeutic device represented in FIGS. 16 and 17 differs from that represented with reference to FIGS. 12 to 15 only insofar as the expandable medicinal sleeve 7, and also the expandable connection sleeve 10, comprise a plurality of radial channels 9 running from the outside toward the inside of the substrate, in such a way as to permit and promote the passage of the bodily liquids or secretions, contributing to or increasing the expansion of the hydrophilic material. These radial channels are also provided in the protective surface envelope 11, both on the upper tubular element 3 and on the lower tubular element 14.

The therapeutic device represented with reference to FIGS. 18 and 19 differs from that represented with reference to FIGS. 12 to 15 only insofar as it comprises a sheath 8 of a synthetic foam, which is both compressible and radially expandable, between the medicinal sleeve 7 proper and the core 6 of the upper tubular element 3. With the exception of the medicinal sleeve 7, the same arrangement is used for the outer sleeve 17 of the lower tubular element 14.

A therapeutic device 1 according to the present invention can be placed in the urethra 2 exactly in the same way as that described in document WO-A-94/18907, and in particular with the insertion assemblies and systems described in that document. These means or devices for non-traumatic insertion are withdrawn as soon as the therapeutic device according to the present invention has been inserted in the urethra.

Figure 20:
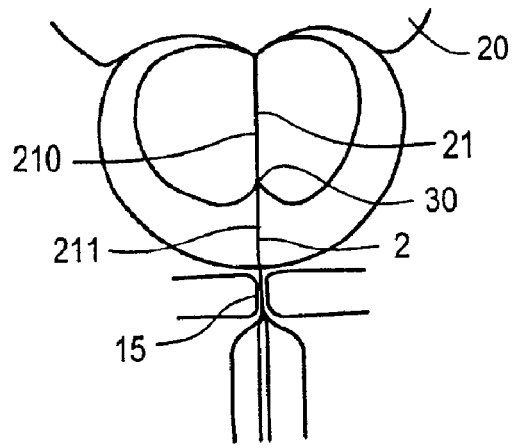
Figure 21:
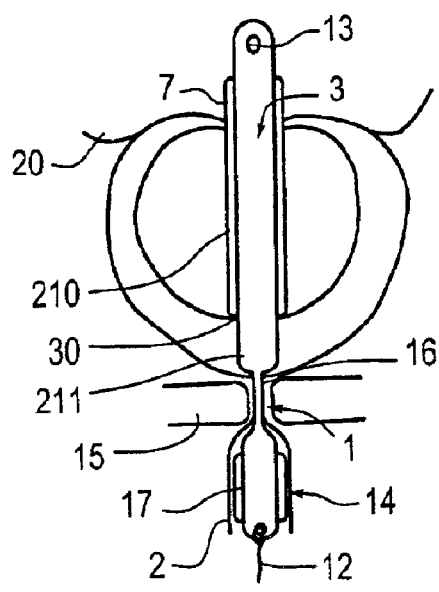
Figure 22:
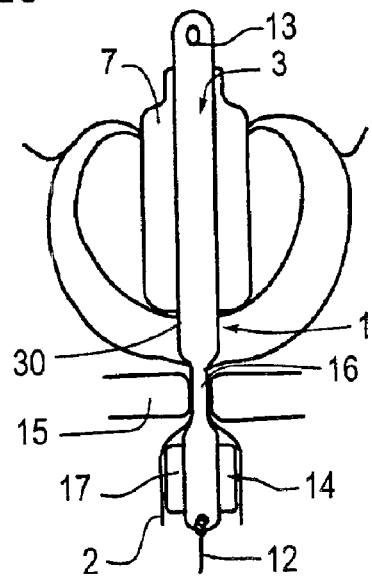

Starting with the urethra as represented diagrammatically before implantation in accordance with FIG. 20, and with a therapeutic device according to the invention in accordance with FIGS. 2 to 7, the therapeutic treatment of the prostatic adenoma is effected in the following manner.

After non-traumatic insertion, the therapeutic device 1 is positioned relative to the sphincter 15 by means of simple traction on the securing thread 12. The correct positioning of the therapeutic device can be checked by ultrasound via the intrarectal route. This leads to the position represented in FIG. 21.

Upon contact with the natural secretions, the therapeutic device is activated, and the surface envelope 11 covering the medicinal sleeve 7 breaks up upon direct contact with the urethra, so that the urethra and then the adenoma thus come into direct contact with the outer surface of said sleeve 7. The same is true as regards the lower sleeve 17.

Consequently, the sleeves 7 and 17 expand simultaneously along their entire length in the area of the lower and upper tubular elements 14 and 3, respectively. This expansion of the sleeve 7 increases the contact surface between the latter and the prostatic urethra, and at the same time the pressure in the area of the adenoma behind the urethral mucosa. The expansion of the sleeve 17 increases its cross section in the bulbar urethra and improves the longitudinal stability or self-stabilizing of the therapeutic device according to the present invention. This therefore leads to the configuration of the device as represented in situ in FIG. 22.

The erosion of the urethra 2 and then of the adenoma gradually progresses along a substantially cylindrical surface front which is centered on the medicinal sleeve 7, while the mechanical contact with the outer surface of the medicinal sleeve 7 allows the cytoreductive agent to exert its chemical effect on the surrounding tissues. Once the erosion has progressed so far as to give a cavity whose cross section is substantially equal to that of the sleeve 7, the contact between the cytoreductive agent and the tissues disappears and the therapeutic effect ceases.

From this moment, the urine easily seeps between the sleeve 7 and the tissues in order to impregnate the hydrophilic substrate, which may additionally be biodegradable, for example under the effect of a modification of the pH of the urine. The same degradation is observed in respect of the sleeve 17. Consequently, the hydrophilic substrate breaks down, so as to give the configuration represented in FIG. 23.

Finally, the therapeutic device can be withdrawn as soon as it is desired that the therapeutic effect cease, or when the latter has become non-existent on account of the absence of contact between the tissues and the medicinal sleeve 7. The withdrawal of the device 1 is possible by means of simple traction on the securing thread 12, so as to result in the totally treated urethra in accordance with FIG. 24.

If a device in accordance with FIGS. 8 and 9 is used, the expansion phase is omitted.

If a device in accordance with FIGS. 18 and 19 is used, the phase of absorption of the sleeves 7 and 17 is omitted.

The use of a therapeutic device according to the invention affords a high degree of safety, both passive and active.

With regard to passive safety, as far as the bladder 20 is concerned there is no direct contact between the medicinal sleeve 7 and the wall of the bladder. Supposing that a part of the sleeve 7 emerges into the bladder and bathes in the urine, in the absence of friction with the tissues the protective envelope 11 will not be broken down or degraded, which fact prevents the release of the cytoreductive agent; and, by depositing on this envelope, the salts contained in the urine form a supplementary protective layer.

With regard to passive safety in the area of the sphincter, it will be noted, in accordance with the above description, that the latter is situated more than 10 mm from the medicinal sleeve 7. The segment 211 inferior to the verumontanum is not intubated by the medicinal sleeve 7 and represents a safety barrier for the sphincter 15. The bulbar urethra is never in contact with the medicinal sleeve 7, except momentarily upon insertion of the device 1. The cytoreductive effect cannot pass deep into the prostate since, as has already been stated, it is a contact effect; the latter is limited in terms of depth by the cross section of the medicinal sleeve 7, in its expanded configuration.

With regard to active safety, the means for checking the correct positioning of the device 1 are:

for the physician, at the moment of positioning or during a follow-up check, intrarectal and suprapubic ultrasound, for example; later, the degree of absorption can be evaluated by measuring the diameter of the medicinal sleeve by means of radiography;

for the patient, the thread 12 and its indicator 50 emerging at the level of the meatus 18 allow him to check, upon each miction, whether the device is in the correct position; its disappearance may cause him to fear an upward migration, demanding an immediate medical check, and its downward migration will lead to dysuria or leakage of urine, likewise demanding a medical check.

All in all, the thread 12 has a triple role:

positioning of the device just after insertion;

indication of the correct positioning of the device, throughout the period of treatment;

and means for withdrawing the device at the end of treatment.

It will be possible to prevent any infection by means of incorporating a bacteriostatic agent in the medicinal sleeve 7.

A device according to the invention furthermore affords an optimal cost/efficacy ratio, for the following reasons.

The treatment does not require any heavy external instrumentation, since the positioning can be performed without general anesthesia, using a simple anesthetic contact gel in the urethra. And simple intrarectal ultrasound makes it possible to check that the therapeutic device is correctly positioned.

The morbidity associated with the therapeutic device is much lower than that associated with surgery and amounts to no more than perineal discomfort and transitory aggravation of the prostatism. However, the morbidity will at any rate be limited to the time necessary for the action of the therapeutic device, since the latter is in place on a temporary basis.

In terms of efficacy, with a device according to the invention, a cavity of suitable shape is created, for example cylindrical, inside the prostate, with a result approximating to that which can be obtained by surgery.

In all, the invention succeeds in combining maximum efficacy (that of surgery), with minimal morbidity (that of a medicament), for a low cost (that of a prosthesis).

According to the present invention, the therapeutic device can have a single size, since a length of the upper tubular element of the order of 70 mm allows the majority of prostatic obstructions to be treated.

The medicinal sleeve can incorporate chemical compounds which are non-cytostatic, non-cytolytic, such as alpha-blockers, enzyme inhibitors, enzymes or hormones, with a view to reducing the exposure of the overall organism to these therapeutic agents and to reducing their morbidity, while at the same time maintaining a satisfactory efficacy.

In accordance with FIGS. 26 and 27, the medicinal sleeve 7 and the internal core 6 are off-centered in relation to each other in such a way as to destroy the proliferating cells in preferential directions.

A therapeutic device according to the invention also offers the following alternatives:

the flexible connection sleeve 16 between the tubular elements 3 and 14 can be perforated, in a manner distributed about its perimeter, especially by longitudinal slots or windows;

the tubular elements 3 and 14 form together with the sleeve 16, in its flow configuration, a conduit which has an internal cross section which is substantially constant along the longitudinal direction of the device;

the wall of each tubular element 3 and 14, and in particular its core 6, comprises a tubular reinforcement frame, in particular a metal or non-metal coil, which is for example embedded in the material of each element.

What is claimed is:

1. A therapeutic device intended for substantially fully intracorporeal insertion for treatment of an obstruction in the prostatic portion of a male urethra, comprising:

a non-biodegradable element that is designed to be placed and retained in a prostatic portion of the male urethra to maintain a channel, said element being sufficiently flexible to conform to the urethra, but sufficiently rigid to maintain the channel for urine flow in the prostatic portion, the channel providing for passage of urine from upstream of the obstruction to downstream of the obstruction; and a cytoreductive agent that causes reduction of the obstruction, said cytoreductive agent being positioned along said element, so as to treat the obstruction of the prostatic portion of the male urethra when said element is retained in the prostatic portion of the male urethra, wherein said element comprises a bottom end and a top end, and wherein said cytoreductive agent is positioned between said bottom end and said top end of said element, wherein said top end of said element is blind, and includes at least one perforation in order to ensure the passage of urine, and wherein said device further comprises a withdrawal thread and is non-traumatically removable from the male urethra by said withdrawal thread following treatment of the obstruction.

2. A therapeutic device intended for substantially fully intracorporeal insertion for treatment of an obstruction in a natural lumen through which a fluid naturally flows, comprising:

a non-biodegradable element that is designed to be placed and retained in the natural lumen to maintain a channel, said element being sufficiently flexible to conform to the natural lumen, but sufficiently rigid to maintain the channel for flow of the fluid in the lumen, the channel providing for passage of the fluid from upstream of the obstruction to downstream of the obstruction with respect to natural fluid flow; and a cytoreductive agent that causes reduction of the obstruction, said cytoreductive agent being positioned along said element, so as to treat the obstruction of the natural lumen when said element is retained in the natural lumen, wherein said element comprises a bottom end and a top end, and wherein said cytoreductive agent is positioned between said bottom end and said top end of said element, wherein said top end of said element is blind, and includes at least one perforation in order to ensure the passage of the fluid, and wherein said device further comprises a withdrawal thread and is non-traumatically removable from the natural lumen by said withdrawal thread following the obstruction.

3. A therapeutic device intended for substantially fully intracorporeal insertion for treatment of an obstruction in a natural lumen through which a fluid naturally flows, comprising:

a non-biodegradable element that is designed to be placed and retained in the natural lumen to maintain a channel, said element being sufficiently flexible to conform to the natural lumen, but sufficiently rigid to maintain the channel for flow of the fluid in the lumen, the channel providing for passage of the fluid from upstream of the obstruction to downstream of the obstruction with respect to natural fluid flow;

a cytoreductive agent that causes reduction of the obstruction, said cytoreductive agent being positioned along said element, so as to treat the obstruction of the natural lumen when said element is retained in the natural lumen; and an other element attached to said non-biodegradable element by a flexible connection, wherein said device further comprises a withdrawal thread and is non-traumatically removable from the natural lumen by said withdrawal thread following treatment of the obstruction.

4. The device of claim 3, wherein said other element does not comprise or support a cytoreductive agent.

5. The device of claim 3, wherein said other element comprises a core made of a biocompatible but non-biodegradable material.

6. The device of claim 5, wherein said biocompatible but non-biodegradable material of said other element is silicone rubber.

7. The device of claim 3, wherein at least a portion of said other element is radially expandable.

8. The device of claim 3, wherein said natural lumen is the prostatic portion of a male urethra.

9. A method of treating an obstruction of a natural lumen, comprising inserting said device of claim 3, into the obstructed natural lumen so that said element is positioned in contact with the obstruction, thereby opening the obstructed natural lumen and allowing normal passage of the fluid.

10. The method of claim 9, wherein said cytoreductive agent causes a reduction in the obstruction.

11. The method of claim 10, wherein said cytoreductive agent causes the reduction in the obstruction when in direct contact with the obstruction.

12. The method of claim 11, wherein said cytoreductive agent gradually ceases to cause the reduction in the obstruction as direct contact of said device with the obstruction ceases.

13. The method of claim 10, further comprising removing said device once sufficient reduction has occurred that the natural lumen can function normally in absence of said device.

14. The method of claim 10, wherein the obstruction is a tumoral obstruction.

15. The method of claim 14, wherein said cytoreductive agent erodes the tumoral obstruction.

16. The method of claim 9, further comprising temporarily maintaining said device in the natural lumen and then removing said device from the natural lumen.

17. A therapeutic device intended for being substantially fully located in a natural lumen through which a fluid naturally flows, said fluid flow being controlled by a sphincter through said lumen, said device comprising:

a non-biodegradable tubular bio-active element that is designed to be placed in at least an obstructed part of said natural lumen, upstream of said sphincter, said element having a substantially continuous wall and external surface and being sufficiently flexible to conform to said lumen, but sufficiently rigid to maintain a channel for flow of the fluid in the lumen, said wall being fluid-tight with respect to said natural fluid flow, and said channel providing for passage of the fluid flow from upstream of the obstruction to downstream of the obstruction with respect to said natural fluid flow;

said bio-active element being retained in the downstream direction by said sphincter, and in the upstream direction by retaining means linked to said element and to be placed in said lumen downstream of said sphincter, wherein said retaining means is not therapeutically active;

said bio-active element comprising a therapeutic agent that causes reduction of the obstruction supported by and arranged around and along said element to be delivered by contact between said external surface and said obstruction; and said device being arranged to be inserted into and removed from said lumen in a substantially non-traumatic manner.

18. A device as claimed in claim 17, wherein the lumen is a male urethra and the obstructed part is the prostatic portion of said urethra.

19. A device according to claim 17, wherein the therapeutic agent is a cytoreductive agent.

20. The device according to claim 17, wherein said natural lumen is the prostatic portion of a male urethra.

21. A therapeutic device intended for being substantially fully located in a natural lumen through which a fluid naturally flows, said fluid flow being controlled by a sphincter through said lumen, said device comprising:

a non-biodegradable tubular element that is designed to be placed in at least an obstructed part of said natural lumen, upstream of said sphincter, said element having a substantially continuous wall and external surface and being sufficiently flexible to conform to said lumen, but sufficiently rigid to maintain a channel for flow of the fluid in the lumen, said channel providing for passage of the fluid flow from upstream of the obstruction to downstream of the obstruction with respect to said natural fluid flow;

said element being retained in the downstream direction by said sphincter, and in the upstream direction by retaining means linked to said element and to be placed in said lumen downstream of said sphincter;

said element comprising a therapeutic agent that causes reduction of the obstruction supported by and arranged around and along said element to be delivered by contact between said external surface and said obstruction; and said device being arranged to be inserted into and removed from said lumen in a substantially non-traumatic manner, said device comprising a withdrawal thread at its downstream end, arranged for the non-traumatic removal of said device.

22. A method of treating an obstruction of a natural lumen, comprising inserting said device of claim 17 into the obstructed natural lumen so that said element is positioned in contact with the obstruction, thereby opening the obstructed natural lumen and allowing the normal passage of the fluid.

23. A method for treating an obstruction in the prostatic portion of a male urethra, comprising inserting said device of claim 20 into the obstructed portion of the male urethra, thereby opening the obstructed urethra and allowing normal passage of urine.

24. A method for treating an obstruction prostatic portion of a male urethra, comprising inserting said device of claim 8 into the obstructed portion of the male urethra, thereby opening the obstructed urethra and allowing normal passage of urine.

* * * * *